US010791778B2

(12) United States Patent
Williams et al.

(10) Patent No.: US 10,791,778 B2
(45) Date of Patent: Oct. 6, 2020

(54) STRESS REDUCING POLYMERIC GLOVE

(71) Applicant: ANSELL LIMITED, Richmond (AU)

(72) Inventors: Jali Lamar Williams, Tanjung Kling (MY); Sze Yin Ng, Semabok (MY); David Mark Lucas, Petaling Jaya (MY); Azman Hamzah, Melaka (MY)

(73) Assignee: Ansell Limited, Victoria (AU)

( * ) Notice: Subject to any disclaimer, the term of this patent is extended or adjusted under 35 U.S.C. 154(b) by 111 days.

(21) Appl. No.: 16/063,319

(22) PCT Filed: Jan. 18, 2017

(86) PCT No.: PCT/AU2017/000008
§ 371 (c)(1),
(2) Date: Jun. 18, 2018

(87) PCT Pub. No.: WO2017/124134
PCT Pub. Date: Jul. 27, 2017

(65) Prior Publication Data
US 2018/0360143 A1 Dec. 20, 2018

Related U.S. Application Data

(60) Provisional application No. 62/280,749, filed on Jan. 20, 2016.

(51) Int. Cl.
*A41D 19/00* (2006.01)
*A61B 42/10* (2016.01)
*B29D 99/00* (2010.01)

(52) U.S. Cl.
CPC ..... *A41D 19/0096* (2013.01); *A41D 19/0062* (2013.01); *A61B 42/10* (2016.02); *B29D 99/0067* (2013.01)

(58) Field of Classification Search
CPC ............ A41D 19/0003; A41D 19/0082; A41D 19/01547; A41D 19/04
USPC ........................ 2/161.1, 161.6, 163, 167–169
See application file for complete search history.

(56) References Cited

U.S. PATENT DOCUMENTS

| 1,097,018 | A | * | 5/1914 | Hadfield | ............ | A41D 19/0062 2/168 |
| 2,036,413 | A | * | 4/1936 | Herbruck | ........... | A41D 19/0062 2/168 |
| 4,441,213 | A | | 4/1984 | Trumble et al. | | |
| 5,323,490 | A | * | 6/1994 | Yarbrough | ......... | A41D 19/0062 2/161.7 |
| 6,760,923 | B1 | | 7/2004 | Tate | | |
| 9,179,718 | B2 | * | 11/2015 | Anstey | .................. | A61B 42/00 |
| 2002/0166156 | A1 | * | 11/2002 | Clark | ................. | A41D 19/0062 2/161.7 |

(Continued)

FOREIGN PATENT DOCUMENTS

| CN | 104619206 A | 5/2015 |
| JP | 09215810 A | 8/1997 |
| KR | 2019980057217 U | 10/1998 |

OTHER PUBLICATIONS

International Search Report dated Apr. 18, 2017 for PCT Application No. PCT/AU2017/000008.

*Primary Examiner* — Katherine M Moran
(74) *Attorney, Agent, or Firm* — Moser Taboada

(57) ABSTRACT

Polymeric gloves having stress-reducing ridges, and methods and formers for manufacturing polymeric gloves having stress-reducing ridges, are disclosed.

9 Claims, 6 Drawing Sheets

(56) References Cited

U.S. PATENT DOCUMENTS

2013/0291282 A1    11/2013  Anstey
2015/0189932 A1*  7/2015  Champagne ........... A41D 13/08
                                                             2/161.6
2019/0357609 A1*  11/2019  Williams ........... A41D 19/0072

* cited by examiner

STRESS REDUCING POLYMERIC GLOVE

BACKGROUND

Field of the Invention

The invention is directed to personal protective equipment and, more specifically, to polymeric gloves having stress reducing ridges and formers for manufacturing polymeric gloves having stress reducing ridges.

Description of the Related Art

Polymeric gloves, such as surgical and examination gloves, are made of strong but flexible elastomers, which permit a snug fit to hands. Gloves are often formed in a shape that approximates the shape of a flattened hand. However, gloves made in this shape are not ergonomic. For example, surgeons wearing surgical gloves may do so for long durations during procedures, which tire the surgeon's fingers and/or hands because the elastic modulus of the elastomer, of which the glove is made, must be overcome to flex the fingers. Also, in an attempt to relieve stresses, some wearers use oversized gloves, which unfortunately cause a loss of dexterity and grip. Furthermore, surgeons and other medical personnel often "double-glove" to provide extra barrier protection, leading to increased fatigue for wearers. Polymer scientists have also failed in attempts to create elastomers that are flexible and sufficiently abrasion and puncture resistant.

Polymeric gloves are formed by dipping formers into elastomeric emulsions, which adhere to the formers. The emulsion coagulates as a coating on the formers and, following a heat curing step, the gloves are stripped from the formers. However, prior to complete coagulation, the emulsion remains flowable on the formers and the emulsion may drip or flow, leading to variations in quality and localized differences in thickness. Specifically, glove formers are dipped finger first into elastomeric emulsions and are oven dried. However, such gloves are negatively impacted by material bunching in certain areas, such as the fingertips. This may cause, for example, a lack of tactility at the fingertips. Inverting the former for some designs can cause bunching at the crotches between the fingers and/or index finger/thumb. Also, notably, these attempts were ineffective at demonstrating hand stress reduction for wearers. For example, the inclusion of small sized, tightly dimensioned accordion or corrugated like feature shapes, pleating, or other embodiments from formers having these features resulted in ineffective cleaning of the formers, i.e., residue build up in these types of surface recesses. Rapid residue build up in the features leads to barrier defects such as pinholes, poor wetting, or thin spots on gloves made therewith.

Other attempts to create gloves that alleviate stresses on the hands of wearers have included gloves having bent fingers, which are bent at the knuckles by 30-50 degrees. However, formers having bent fingers exacerbate differences in thickness of the glove, too. The formers having bent fingers, in addition to exacerbating differences in thickness, may also trap air, resulting in unfavorable bubbles in the polymeric gloves, i.e., quality problems.

Therefore, polymeric gloves that can alleviate stresses on wearers without loss of tactility and are easily manufactured represent an advance in the art.

SUMMARY

Embodiments according to the invention include stress reducing polymeric gloves, and methods for manufacturing stress reducing polymeric gloves, substantially as shown in and/or described in connection with at least one of the figures, as set forth more completely in the claims, are disclosed. Various advantages, aspects, and novel features of the present disclosure will be more fully understood from the following description and drawings.

The foregoing summary is not intended, and should not be contemplated, to describe each embodiment or every implementation of the present invention. Other and further embodiments of the present invention are described below.

BRIEF DESCRIPTION OF THE DRAWINGS

So that the manner in which the above recited features of the present invention can be understood in detail, a more particular description of embodiments of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is to be understood that elements and features of one embodiment may be in other embodiments without further recitation. It is further understood that, where possible, identical reference numerals have been used to indicate comparable elements that are common to the figures.

DETAILED DESCRIPTION

Figure 1:
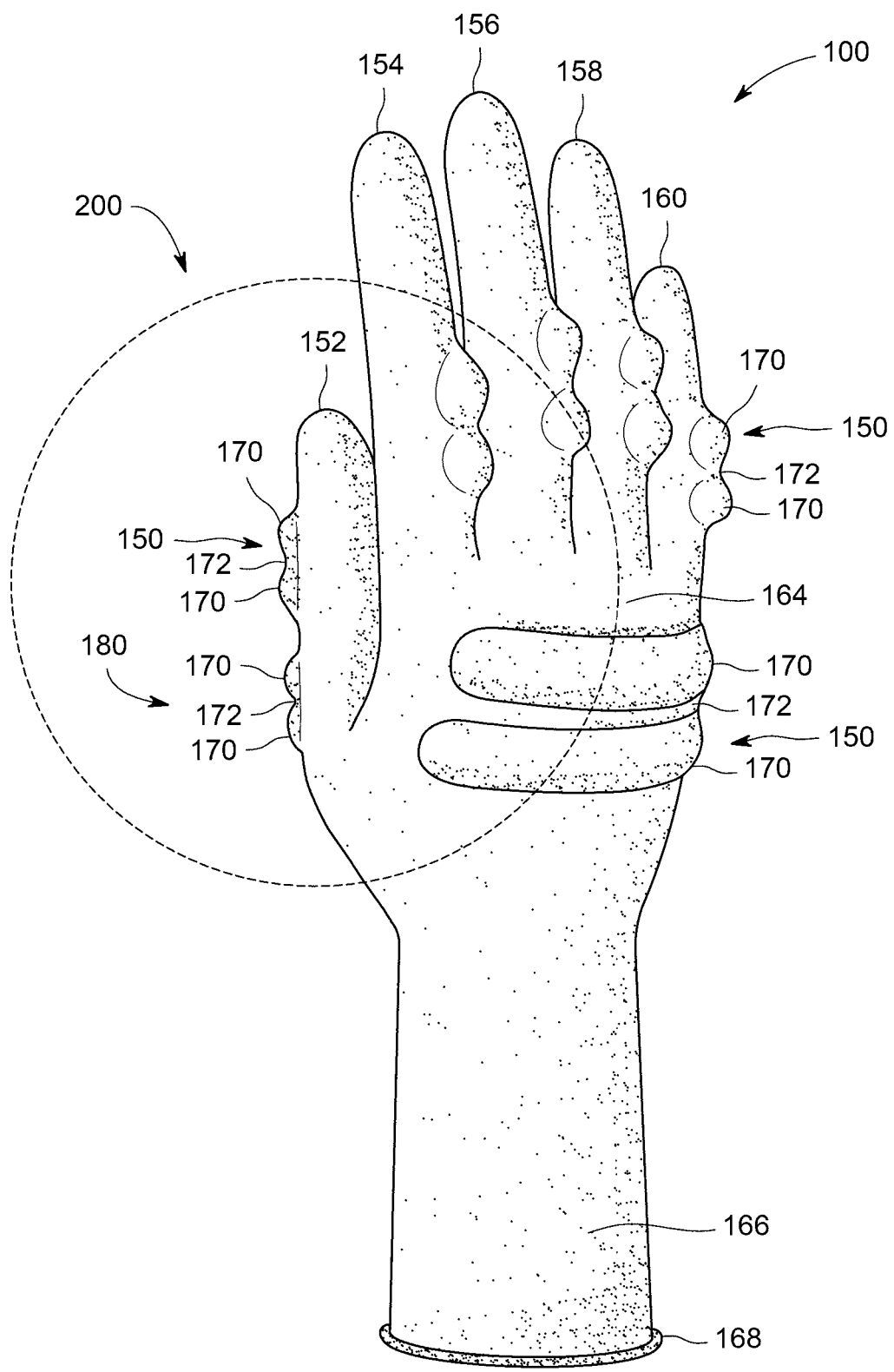
FIG. 1 depicts a perspective view of a polymeric glove having stress-reducing ridges, according to embodiments of the invention.

Embodiments of the invention comprise polymeric gloves, such as examination gloves, surgical gloves, industrial gloves, and gloves for household use that comprise ridges for stress reduction in specific areas. For example, specific areas can correspond to joints of the human hand, such as those between, for example, a distal phalange bone and a middle phalange bone, and/or between a middle phalange bone and a proximal phalange bone and/or the like. In this manner, polymeric gloves can be made to reduce stresses on the human hand during flexing. Additionally or alternatively, polymeric gloves can be made to reduce stresses during prolonged periods of use while remaining tight and snug where needed, e.g., fingertips. Furthermore, the embodiments of the polymeric gloves comprising the stress reducing ridges permit the use of elastomers having a high elastic modulus. Specifically, because the stress reducing ridges allow the reduction of stress to the hands of a wearer during use, stronger elastomers can be used for enhanced barrier properties, i.e., enhanced chemical resistance, abrasion resistance, and/or puncture resistance. The inventors have unexpectedly discovered that thicker stress-reducing ridges and thicker polymeric gloves, which are also within the scope of all embodiments according to the invention and which can be combined with all other embodiments described herein may be provided while maintaining flexibility and fit. Thicker gloves are typically less flexible but more puncture resistant, however, thicker polymeric gloves having stress-reducing ridges according to the invention described herein are sufficiently flexible for medical use, for example. Any, all, or some of the embodiments according to the invention comprise polymeric gloves having stress-reducing ridges that are, for example, 0.10-0.30 mm in cross-sectional thickness. Some embodiments according to the invention comprise polymeric gloves having stress-reducing ridges that are 0.15-0.20 mm in cross-sectional thickness. Exemplary embodiments according to the invention may further comprise polymeric gloves having stress-reducing ridges that are 0.16-0.17 mm in cross-sectional thickness.

Embodiments according to the invention comprise a polymeric glove that includes a thumb having a front surface and a back surface; a plurality of fingers, each of the plurality of fingers having a front surface and a back surface; and a backhand region having a back surface, wherein at least one stress-reducing ridge is formed on at least one of the back surfaces of the thumb, the backhand region, and/or at least one of the back surfaces of at least one of the plurality of fingers. Embodiments of the invention further comprise polymeric gloves having stress-reducing ridges on a surface, such as a surface on a backhand region, e.g., a carpus area of a human hand.

Before describing embodiments of the present invention in detail, the terminology used herein is for the purpose of describing particular embodiments only, and is not intended to be limiting. The invention should not necessarily be limited to specific compositions, materials, designs or equipment, as such may vary. All technical and scientific terms used herein have the usual meaning conventionally understood by persons skilled in the art to which this invention pertains, unless context defines otherwise. Also, as used in this specification and the appended claims, the singular forms "a," "an," and "the" include plural referents unless the context clearly dictates otherwise.

The term "stress-reducing ridge" refers to any of the ridges described herein. A ridge or stress-reducing ridge may comprise a single peak or a plurality of peaks. A plurality of peaks may have valleys disposed therebetween.

The term "flexing" or "flex" refers to finger movements, such as bending fingers, making a fist, gripping, grasping, clenching or otherwise folding the fingers.

The terms "emulsion," "dispersion," and "suspension" are generally analogous and indicate a system in which small particles of a substance, such as rubber particles, are mixed with a fluid (such as water and/or alcohols and/or other organic fluids) but are at least partially undissolved and kept dispersed by agitation (mechanical suspension) and/or by the molecular forces in a surrounding medium (colloidal suspension). Emulsions contemplated herein may further comprise typical and suitable components for rubber or elastomeric formulations and compounds, such as accelerators, such as guanidines, thiazoles, thiurams, sulfenamides, thioureas, dithiocarbamates, and xanthanates. Emulsions contemplated herein may further comprise, surfactants, such as sodium dodecyl sulfates and polyvinyl alcohols. Emulsions contemplated herein may further comprise activators, such as zinc oxides, cross-linking agents and curatives, such as elemental sulfur and/or polysulphidic donors. Emulsions contemplated herein may further comprise anti-oxidants, anti-ozonants, rheology-modifiers, such as various clays and aluminosilicates, pH adjusters, such as hydroxides, such as potassium hydroxide, pigments, processing agents, and/or fillers as are known to those in the art.

The term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" includes all possible geometrical configurations of the molecule. These configurations include, but are not limited to isotactic, syndiotactic and random symmetries.

The term "thermoplastic" generally includes polymer materials that become reversibly pliable, moldable, and heatable above a specific temperature and solidify upon cooling. The term "thermoset" generally includes are polymer materials that strengthen following heating and solidification, but cannot be successfully remolded or reheated after an initial heat-forming. The term "thermoplastic elastomer" (TPE) are a class of copolymers comprising both thermoplastic and elastomeric/thermoset materials properties and generally have crosslinking between adjacent polymeric molecular chains. The term "rubber" generally indicates elastomers produced from natural rubber latexes or synthetic elastomers.

Exemplary thermoplastics include, without limitation, polychloroprenes, butyl rubbers, natural rubber, synthetic polyisoprenes, poly(vinyl) chlorides, polyesters, polyamides, polyfluorocarbons, polyolefins, polybutadienes, polyurethanes, polystyrenes, poly(vinyl) alcohols, and copolymers of the foregoing, and elastomeric polymers such as elastic polyolefins, copolyether esters, polyamide polyether block copolymers, block copolymers having the general formula A-B-A' or A-B like nitrile-butadiene rubber (NBR), styrene-poly(ethylene-propylene)-styrene, styrene-poly(ethylene-butylene)-styrene, (polystyrene/poly(ethylene-butylene)/polystyrene, poly(styrene/ethylene-butylene/styrene), copoly(styrene/ethylene-butylene), A-B-A-B tetrablock copolymers and the like and blends of any of the foregoing.

FIG. 1 depicts a perspective view of a polymeric glove 100 having stress-reducing ridges 150, according to embodiments of the invention. The polymeric glove 100 comprises a thumb 152, a plurality of fingers 154, 156, 158, 160, a palm region (not shown in this view), and a backhand region 164. The polymeric glove 100 may further include a cuff 166. Any of the thumb 152, any of the plurality of fingers 154, 156, 158, 160, the palm region, the backhand region 164, and/or the cuff 166 may comprise one or more stress-reducing ridges 150. As depicted, according to some embodiments of the invention, the polymeric glove 100 may also include a lower ridge 180 on the thumb 152. The polymeric glove 100 optionally includes a bead 168 proximate an opening, for receiving a human hand, of the polymeric glove 100. The polymeric glove 100, shown in FIG. 1 further comprises at least one stress-reducing ridge 150. The at least one stress-reducing ridge 150, or any and all other stress-reducing ridges described herein, can be provided on the thumb 152, the plurality of fingers 154, 156, 158, 160, and/or the backhand region 164. According to some embodiments, which can be combined with other embodiments described herein, the stress-reducing ridge 150 comprises two peaks 170 and a valley 172 disposed between the two peaks 170. In other embodiments, which can be combined with any and all other embodiments described herein, the stress-reducing ridge 150 can include a single peak 170. The stress-reducing ridges 150 may be disposed on one or more regions of the polymeric glove 100 corresponding with a distal interphalangeal joint, a proximal interphalangeal joint and/or a metacarpophalangeal joint of a hand of a wearer of the polymeric glove 100.

The stress-reducing ridges 150, as with other ridges described herein, provide additional glove material at the joints so that a person wearing the polymeric glove 100 may open and close the hand, i.e., flex, without having to significantly stretch the glove material. In other words, repeated flexing does not easily tire a hand, e.g., the material in areas of the polymeric glove 100 corresponding to the joints, wherein stress on the wearer is reduced. For example, a polymeric glove 100 having a stress-reducing ridge 150 on a finger, in which the stress-reducing ridge 150 is approximately 4.5 cm×1.0 cm, gives a surface area of approximately 4.5 sq. cm, as compared with a corresponding area of a finger having no ridge. A finger having no ridge would have a surface area of 3 cm×1 cm, i.e., 3.0 sq. cm, i.e., in an approximate 50% difference in surface area per finger. According to some embodiments, which can be combined with other embodiments described herein, the surface area of a stress-reducing ridge 150 may result in an increase of the surface area of 30% to 70% as compared to a surface area without the stress-reducing ridge 150. Similarly, the back of the hand adds approximately an additional 20% to 40% of surface are, or, for some exemplary embodiments, approximately 33% greater surface area. For example, a polymeric glove 100 having no stress-reducing ridge 150 on the backhand region 164 would have a surface area of approximately 3 cm×6.5 cm, i.e., 19.5 sq. cm, while a stress-reducing ridge 150 on the backhand region 164 would have a surface area of approximately 29.25 sq. cm (4.5 cm×6.5 cm). It should be noted that the foregoing surface areas are for a size 7.5 polymeric glove and the stress-reducing ridges 150 may be made larger or smaller, resulting in even greater surface area differences for gloves of differing sizes having stress-reducing ridges. Some, any, or all stress reducing ridges, according to embodiments of the invention as disclosed herein, comprises single or multiple enlarged bulbous protrusions, i.e., peaks (described more fully below), on at least one of the surfaces of the backhand region or at least one of the surfaces of at least one of the plurality of fingers. The stress-reducing ridges 150 facilitate effective cleaning of the formers used to produce the polymeric gloves 100, wherein barrier defects caused by the addition of the protrusions are eliminated.

In the case of multiple protrusions, an (n−1) number of valleys will separate multiple peaks, displaying an undulating appearance to the stress-reducing ridge 150. The single ridge or two ridges and a valley combination are oriented such that a longitudinal axis of the stress-reducing ridge 150 and/or valley may run either perpendicular or parallel to the longitudinal axis of the polymeric glove 100, i.e., an axis extending from the cuff to the fingertips.

Figure 2:
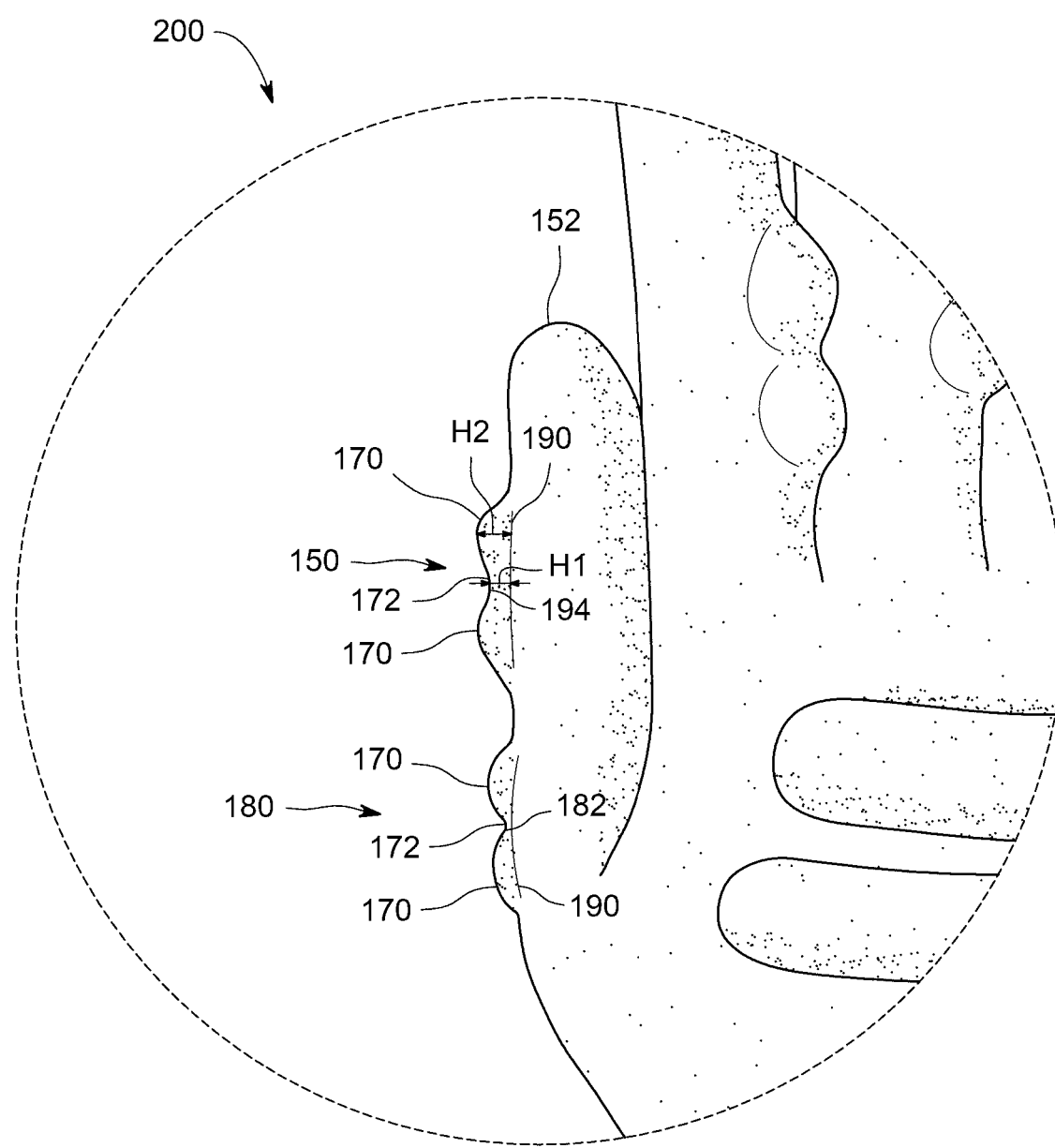
FIG. 2 depicts a close up view of two stress-reducing ridges disposed on a polymeric glove, according to embodiments of the invention.

FIG. 2 depicts a close up view of two stress-reducing ridges 150, 180 disposed on a polymeric glove 100, according to embodiments of the invention. In some embodiments according to the invention, the valley 172 of the lower ridge 180 has a basepoint 182 that is at the same height with respect to the reference line 190. Alternatively, the shallow basepoint 194 of the valley 172 is disposed higher than the reference line 190 of the peaks 170, as shown with respect to stress-reducing ridge 150. For example, embodiments according to the invention of the polymeric glove 100 comprise a stress-reducing ridge 150 having a baseline 194 that is higher than a reference point, e.g., that is approximately 2 to 8 mm higher than the reference line 190, as denoted by height H1 and, in some exemplary embodiments, is approximately 6 mm higher than the reference line 190. Height H2, which is the distance between the reference line 190 and the peak 170, may be approximately 4-14 mm and, in some exemplary embodiments, approximately 10 mm. In other words, the reference line 190 is a surface of the polymeric glove 100 if the polymeric glove 100 had no stress-reducing ridge. Polymeric gloves, such as the polymeric glove 100, that comprise a stress-reducing ridge, e.g., stress-reducing ridge 150, or 180, have a curved length across the at least two peaks and the valley disposed therebetween as described further below with respect to glove formers used to make the polymeric glove 100. The curved length along the stress-reducing ridge 150, 180 of the polymeric glove 100 is increased by approximately 30-70%. In some exemplary embodiments, the curved length along the stress-reducing ridge 150, 180 is 50% larger compared with a glove having no ridge, e.g., 4.6 cm versus 3.1 cm, wherein the distal interphalangeal joint, proximal interphalangeal joint and/or metacarpophalangeal joint of a hand of a wearer wearing the polymeric glove 100 can flex without having to significantly stretch the elastomeric material of which the polymeric glove 100 is made.

Embodiments according to the invention further include a polymeric glove 100 that comprises a stress-reducing ridge having one peak 170 and no valley, two peaks and one valley, or more than two peaks 170, for examples, three peaks 170, between which are two valleys (not shown in this view). A ridge, such as a stress-reducing ridge 150, as described herein, having three peaks 170 and two valleys may also be disposed on any of the plurality of fingers 154, 156, 158, 160, the backhand region 164 and/or the thumb 152.

Figure 3:
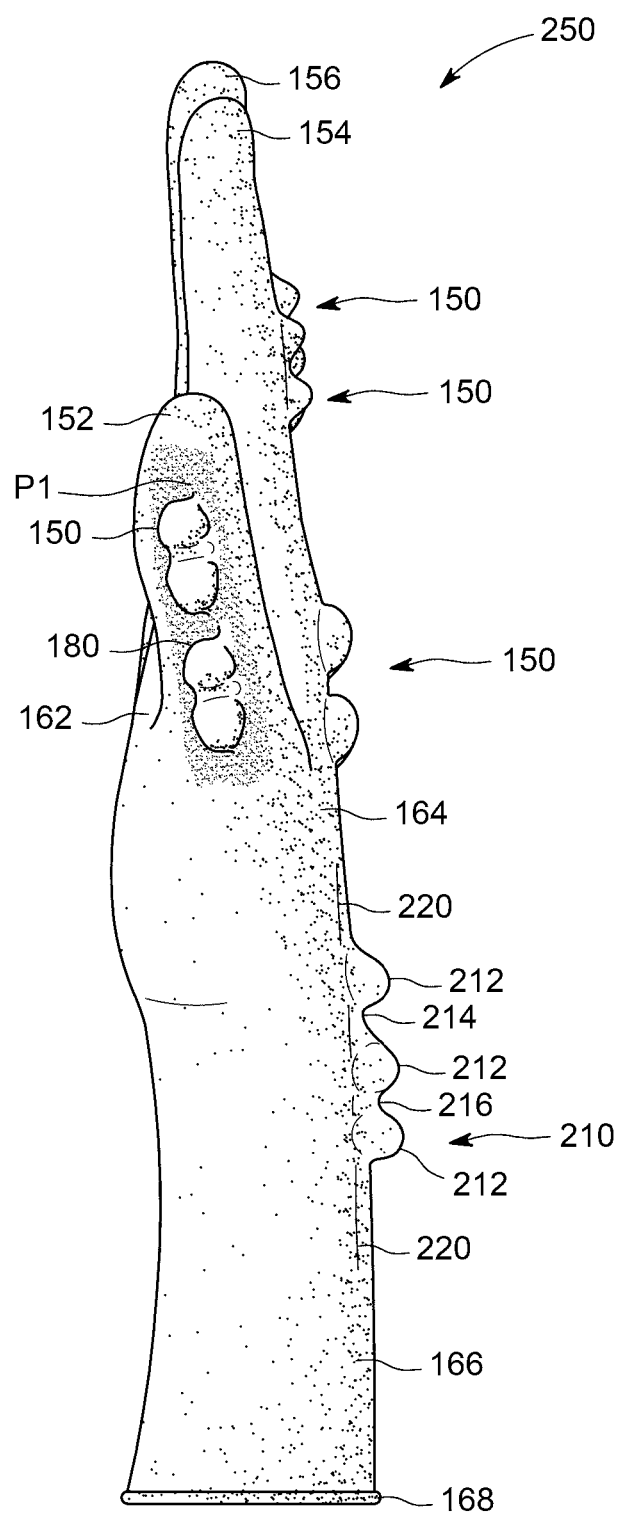
FIG. 3 depicts a left plan view of a polymeric glove having stress-reducing ridges, according to embodiments of the invention.

FIG. 3 depicts a left plan view of a polymeric glove 250 having stress-reducing ridges 150, 180, according to some embodiments of the invention. The left plan view of the polymeric glove 250 shows a middle finger 156, an index finger 154, a thumb 152, a backhand region 164, a palm region 162, a cuff 166, and a bead 168. The polymeric glove 250 depicts the stress-reducing ridge 150 and the lower ridge 180 on the thumb 152. As shown, the stress-reducing ridges 150 and 180 on the thumb 152 of the polymeric glove 250 are not coplanar with the stress-reducing ridges 150 disposed on the index finger 154 and the middle finger 156. In other words, the knuckles of the fingers of a human hand bend in the same plane as each other although the knuckles of a human thumb do not because the thumb is opposed to the fingers. According to some embodiments, which can be combined with other embodiments described herein, one or more ridges on a thumb can be provided in a first plane and one or more ridges in fingers are provided in a second plane different from a first plane. In some embodiments, a plane, formed on a face P1 (depicted as a darkened area) of a thumb 152 is between approximately 50-80 degrees with respect to a plane formed by the plurality of fingers 154, 156, 158, 160, such as the index finger 154 and the middle finger 156. The polymeric glove 250 further illustrates modifications and/or additions to various embodiments of the invention b including a double ridge 210 having three peaks 212, disposed between which are valleys 214 and 216. As an additional optional modification, a valley 214, i.e., one of the valleys, is closer to a reference point 220 than the valley 216, i.e., another one of the valleys, much as described above. The double ridge 210, as shown, may be disposed on the polymeric glove 250 in an area proximal to the metacarpal (wrist) bones of a human hand.

Figure 4:
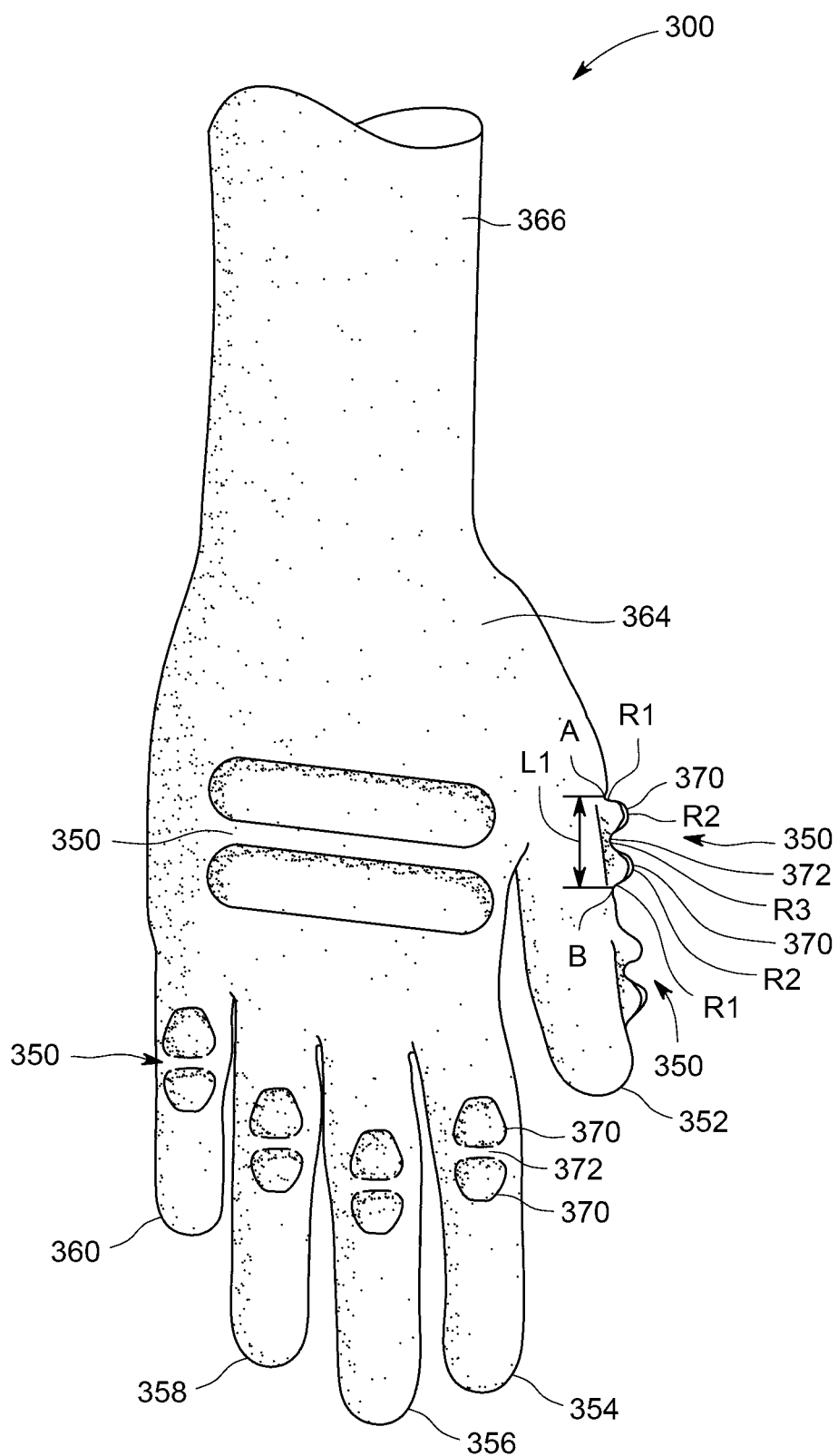
FIG. 4 depicts a glove former having ridge forming feature, according to embodiments of the invention.

FIG. 4 depicts a glove former 300 having ridge forming feature 350, according to embodiments of the invention. The glove former 300 and a glove made therefrom are negatives of each other. The glove former 300 includes at least one ridge forming feature(s) 350. The glove former 350 can further comprise a thumb former 352, a plurality of finger formers 354, 356, 358, 360, a palm former region 362, a backhand former region 364, and a cuff former area 366. Any of the thumb former 352, any of the plurality of finger formers 354, 356, 358, 360, the palm former region (not shown), and/or the backhand former region 364 may comprise one or more ridge forming features 350. Alternatively and additionally, the cuff former area 366 of the glove former 350 may include one or more ridge forming features 350. The ridge former feature(s) 350 may be disposed on one or more regions corresponding with a distal phalange joint, a middle phalange joint, and/or a proximal phalange joint of a hand of a wearer of a polymeric glove manufactured using the glove former 300.

The ridge(s) 350 further comprise peaks 370 which have a radius of curvature R1, R2, and R3. In some embodiments, the radii of curvature of the peaks 370 may be selected to achieve a maximum linear length balanced with minimal feature depth to aid in cleaning, and more hydrodynamically shaped to reduce the turbulence of the dipping entry and withdrawal. In some embodiments, R1-R3 may range from approximately 5-10 mm. In at least one exemplary polymeric glove and/or former, according to the invention, R1 is approximately 8-9 mm, R2 is approximately 6-7 mm, and R3 is approximately 5-6 mm. In some embodiments, a linear distance L1 on the glove former 300, between points A and B is approximately 3.0-3.2 cm. In some embodiments, a curved distance, traversing a surface along the peaks 370 is approximately 4.5-4.8 cm, thereby representing approximately a 50% greater distance than the linear distance L1, resulting in a reduced flexural force required to flex human joints proximal to the ridges(s) 350 of the polymeric glove(s).

Glove formers, such as the glove former 300, having radii of curvature of this magnitude facilitates manufacturability in addition to enhancing the ergonomics of the polymeric glove made therefrom, i.e., stress reduction during flexing. In other words, the glove former 300 can be cleaned easily, allowing access into, for example, R3. Furthermore, the radius of R3 is hydrodynamically beneficial because of a relative lack of turbulence of the emulsion during dipping and withdrawal, resulting in fewer trapped bubbles, a more even cross-sectional thickness of the polymeric glove, and/or other residue buildup.

It is also to be understood that, according to some or all alternatives of the embodiments of the invention, while the above mentioned glove former 300 comprises two peaks 370 and a valley 372 to manufacture a ridge 350, it is also possible to provide a glove former, e.g., the glove former 350, having a mirror configuration, i.e., two valleys that extend into the glove former with a peak disposed therebetween. Any one or more of the peaks 370 and/or valleys 372 may include the same or similar radius of curvature(s) of the other peaks and valleys described herein. A polymeric glove made therewith would, when stripped from the glove former, need to be inverted, i.e., turned inside out, to produce the same polymeric glove as described above.

Figure 5:
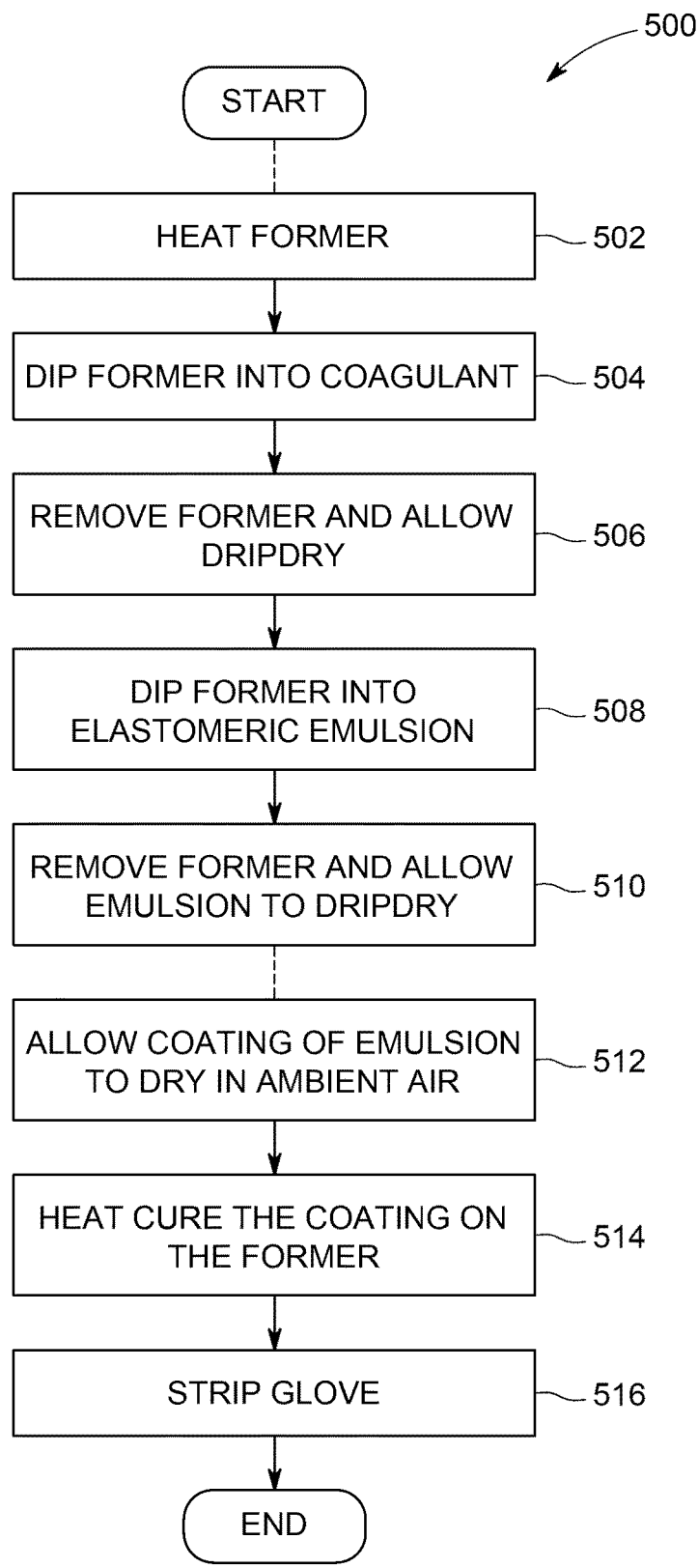
FIG. 5 depicts a flow diagram of a method for manufacturing a polymeric glove having stress-reducing ridges, according to embodiments of the invention.

FIG. 5 depicts a flow diagram for a method 500 for manufacturing a polymeric glove having stress-reducing ridges, according to embodiments of the invention. At step 500, a hand shaped former is provided, which comprises peaks and valleys, which are, for example, the negative (or the positive thereof, in the case of an inverted glove) of the stress reducing ridges on the polymeric gloves discussed above, i.e., the stress-reducing ridges have a radius of curvature that are configured to allow excess coagulant solution or emulsion to drip off in a manner that avoids uneven thickness of both the coagulant and/or emulsion, wherein polymeric gloves formed therewith have consistent wall thicknesses.

The method 500 starts and the former is optionally heated at step 502. At step 504, a coagulant is disposed on the former, such as the coagulant solution described above, e.g., by dipping the former into a bath of the coagulant solution. In at least one embodiment of the invention, the coagulant solution can be heated at a temperature ranging from 42-45° C. At step 506, excess coagulant solution is allowed to drip dry from the former and, optionally, the former is vertically rotated so that the fingers of the former are pointed up and allowed to dry or horizontally rotated with the fingers pointed out and oven dried.

At step 508, the former has a polymeric or elastomeric emulsion or composition disposed thereon, such as by a dipping step, wherein the former is dipped into the emulsion tank, e.g., in a fingers first manner. For example, the temperature of the elastomeric emulsion generally ranges from 15° C.-30° C. At step 510, the former is removed from the emulsion tank and the emulsion is allowed to drip down, i.e., fingers are pointing down, to allow excess emulsion to drip from the former. Allowing excess emulsion to drip from the former promotes the reduction of the thickness of the elastomeric coating formed by the disposition of the emulsion onto the former. Optionally, the former having the elastomeric coating disposed thereon is rotated about a vertical or horizontal axis, optionally while passing through an oven, for drying the coating. At step 512, the coating optionally dries in an oven for several minutes. At step 514, the coating undergoes a curing step to cure the coating, such as within an oven at a temperature of approximately 110-130° C. The curing step may include a duration for approximately ten to twenty minutes. In at least one embodiment according to the invention, the coating is cured in a staged process. For example, at least one exemplary embodiment includes a staged process in which curing occurs at a first stage at 90° C. for fifteen minutes. A second stage may include curing at 100° C. for fifteen minutes. And, for example, a third stage of curing may include heating at 130° C. for fifteen minutes. At step 516, a cured glove having stress reducing ridges is stripped from the former and the method 500 ends. The cured glove may be inverted during stripping or, alternatively, stripped without inverting. Optionally, before the curing step, the elastomeric coating at a distal end from the fingers, i.e., at an open end for receiving a hand, is rolled, e.g., forming a bead, as is known to those in the art.

Some steps of the preceding method 500 may be omitted or performed in a different sequence. For example, additional steps may be employed, such as a subsequent washing step after curing to remove impurities. Optionally, a coating may be foamed and disposed on the former, as above, and is optionally subjected to a salt texturization process, as described below. Also, a second dipping step can provide a second layer of a polymeric coating on any first polymeric coating, wherein either of the first polymeric coating or the second polymeric coating may be foamed.

Embodiments of polymeric gloves manufactured according to the methods disclosed herein comprise an elastomeric material in the shape of a glove that is capable of receiving a human hand, further comprising a thumb having a front surface and a back surface; a plurality of fingers, each of the plurality of fingers having a front surface and a back surface; and a backhand region having a back surface, wherein at least one stress-reducing ridge is formed on at least one of the back surface of the thumb, the backhand region, or at least one of the back surfaces of at least one of the plurality of fingers and wherein a flexing of a human hand wearing the polymeric glove articulates the at least one stress-reducing ridge without having to significantly stretch the polymeric glove. One or more exemplary polymeric gloves may further comprise at least one stress-reducing ridge disposed on each of the plurality of fingers, thumb, and backhand region. Additionally or alternatively, at least one exemplary polymeric glove, according to embodiments of the invention, which can be combined with other embodiments described herein, further comprises at least two peaks and one valley disposed between the two peaks, forming a stress-reducing ridge disposed on each of the plurality of fingers, thumb, and backhand region. Similarly, at least one exemplary polymeric glove further comprises more than one stress-reducing ridge disposed on at least one of the plurality of fingers, thumb, or backhand region. Also, at least one exemplary polymeric glove further comprises more than one stress-reducing ridge disposed on at least one of the plurality of fingers, thumb, or backhand region, wherein at least one of the stress-reducing ridges having two peaks further comprises a baseline of a valley that differs from another baseline of a valley.

Some exemplary polymeric gloves, according to the embodiments of the invention, comprise wherein at least one peak has a radius of curvature of 2-30 mm, and in some embodiments from approximately 6-7 mm, and wherein valley(s) have a radius of curvature of 3-20 mm, and in some embodiments, approximately 5-6 mm, and the base of the peak(s), where there is no valley, has a radius of curvature of 3-30 mm, and, in some embodiments, from 8-9 mm.

Some exemplary polymeric gloves, according to the embodiments of the invention, comprise a ridge or ridges/valley(s), on the backhand region of the glove, that are located 10-45 mm from the baseline of both the index finger and the pinky finger crotches. Also, the backhand ridge or ridges/valley(s) may be inclined from 5-40 degrees from the index finger to the pinky finger.

Some exemplary polymeric gloves, according to the embodiments of the invention, comprise a ridge or ridges/valley(s) on the back surfaces of the fingers, which may be located within a range of 10-75 mm from the finger crotch, and, for some embodiments, approximately 20-40 mm from the individual finger crotch when measured furthest from the ridge. Also, in some embodiments, the location of such a ridge falls within a range of 25-75% of the individual finger length.

Some exemplary polymeric gloves, according to the embodiments of the invention, comprise a ridge having a curved length across the at least one or more peaks and the optional valley(s) disposed therebetween that is increased by 10-85%, and, in at least one embodiment, approximately 48-55% compared with a polymeric glove having no ridge.

Some exemplary polymeric gloves, according to the embodiments of the invention, comprise a stress-reducing ridge or ridges/valley(s) formed on a finger, providing an additional 0.5 sq. cm-10 sq. cm, and, in at least one embodiment, approximately 1.5 sq. cm-3.0 sq. cm of surface area to the back surface of the finger.

Some exemplary polymeric gloves, according to the embodiments of the invention, comprise at least one stress-reducing ridge formed on a backhand region that provides an additional 3 sq. cm-30 sq. cm, and, in at least one embodiment, approximately 10 sq. cm-14 sq. cm of surface area to the backhand region.

Figure 6:
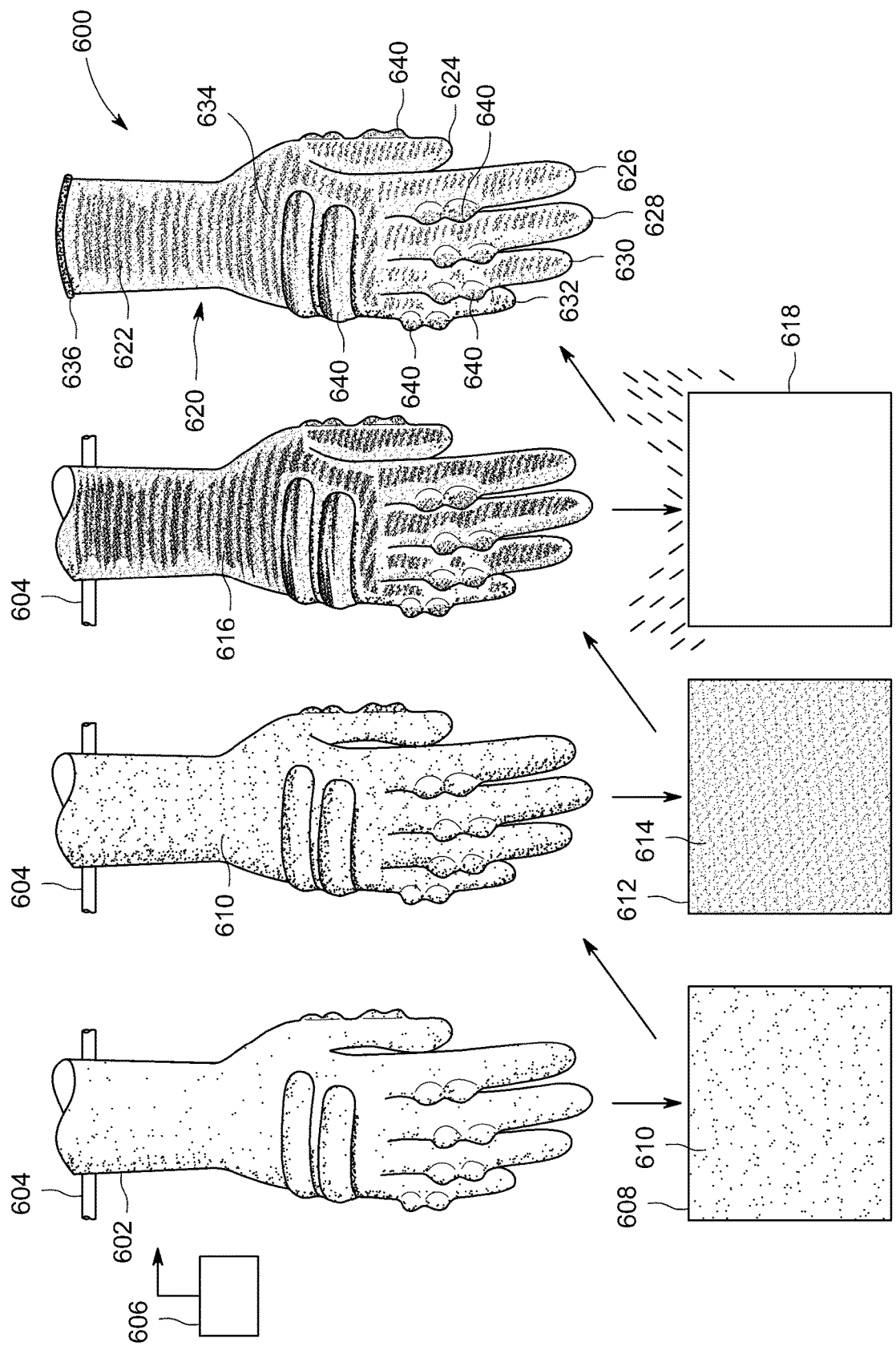
FIG. 6 depicts an apparatus for forming a polymeric glove having stress-reducing ridges, according to embodiments of the invention.

FIG. 6 depicts an apparatus 600 for forming a polymeric glove having stress-reducing ridges, according to embodiments of the invention. A former 602, substantially as described above, i.e., having fingers, a thumb, and at least one peak and no valley or, alternatively, two peaks and a valley disposed between the at least two peaks is provided along a conveyor 604. The conveyor may be controlled by a controller 606 for controlling the movement of the former(s) 602 and the conveyor 604. The former 602 has a ridges (i.e., radius of curvature), as described above, configured to allow excess coagulant solution or polymeric emulsion to drip off in a manner that avoids uneven thickness of both the coagulant solution and/or polymeric emulsion.

The former 602 is dipped into a tank 608 containing a coagulant solution 610 as described above. The former 602 is removed. The former 602 may be oven dried, leaving a coagulant coating on the former 602. The conveyor 604 may allow the former 602 to drip dry with, e.g., the fingers pointing downward and/or rotate so that the fingers are pointed upward. The former 602 is next dipped into a tank 612 having an elastomeric emulsion 614, as described above, therein. The former 602 is then removed and the elastomeric emulsion 614 oven dried on the former 602, leaving an elastomeric coating 616 on the former 602. The former 602 again may be pointed downward followed by rotation so that the fingers are pointed upward. The former 602 is next delivered to an oven 618 so that the elastomeric coating 616 on the former 602 is heated and cured, forming a glove 620, which comprises a shape that is, e.g., the negative of the former 602. The glove 620 is then stripped from the former 602. As shown, the glove 620 comprises a cuff 622, a thumb 624, a plurality of fingers 626, 628, 630, 632, a backhand region 634, a bead 636, and a palm region (not shown). As shown, the glove 620 may include ridges 640 on each of the plurality of fingers 626, 628, 630, 632, the thumb 624, and/or the backhand region 634.

Glove formers, such as the glove formers 300, 602, in accordance with embodiments of the invention may be made of ceramics, borosilicates, metals, plastics, and other suitable materials. Elastomers in accordance with embodiments of the invention comprise natural rubber, synthetic polyisoprene, polychloroprene, butyl rubbers, nitrile-butadienes, highly carboxylated nitrile-butadienes (such as nitrile-butadienes having 35% or greater carboxylation), copolymers of styrene-butadienes, and blends or mixtures thereof.

Embodiments according to the invention comprise the use of a coagulant solution to wet the former and may include an exemplary aqueous solution of 5% calcium nitrate, although other concentrations are possible as are known to those in the art, such as an aqueous solution ranging in concentration from 6-40% calcium nitrate. Other salts, such as calcium chloride, calcium citrate, aluminum sulfate, and the like and/or mixtures thereof may be used. Furthermore, the coagulant solution may be aqueous, alcoholic, or a mixture of aqueous and alcoholic solutions/solvents. Weaker acid solutions may also be used as coagulants, such as formic acid, acetic acid, and other low pKa acids as are known to those in the art.

Embodiments according to the invention comprise the use of salt particles that are optionally embedded into the coating of emulsion before the curing step. Thereafter, removing the salt with a solvent, such as water, either before or after a curing step, provides multi-faceted indentations in the coating, which provide enhanced gripping properties, i.e., salt texturization. The technology of providing enhanced gripping properties via salt embedding and removal is disclosed in commonly-assigned U.S. Pat. Nos. 8,522,363; 7,378,043; 7,771,644; 7,814,570; which are incorporated by reference in entirety.

All numerical values recited herein are exemplary, are not to be considered limiting, and include ranges therebetween, and can be inclusive or exclusive of the endpoints. Optional included ranges can be from integer values therebetween, at the order of magnitude recited or the next smaller order of magnitude. For example, if the lower range value is 0.1, optional included endpoints can be 0.2, 0.3, 0.4 . . . 1.1, 1.2, and the like, as well as 1, 2, 3 and the like; if the higher range is 10, optional included endpoints can be 7, 6, and the like, as well as 7.9, 7.8, and the like.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

It is to be understood that various changes and modifications to the embodiments described herein will be apparent to those skilled in the art. Such changes and modifications can be made without departing from the spirit and scope of the present invention and without demising the attendant advantages. It is, therefore, intended that such changes and modifications be covered by the appended claims.

All references, including publications, patent applications, and patents, cited herein are hereby incorporated by reference to the same extent as if each reference were individually and specifically indicated to be incorporated by reference and were set forth in its entirety herein.

The invention claimed is:

1. A polymeric glove, comprising:
a thumb having a front surface and a back surface;
a plurality of fingers, each of the plurality of fingers having a front surface and a back surface; and
a backhand region having a back surface,
a first stress-reducing ridge disposed across the back surface of the backhand region, wherein the first stress-reducing ridge on the backhand comprises two peaks and one valley disposed between the two peaks; and
at least one additional stress-reducing ridge comprising two peaks and one valley disposed on at least one of the back surfaces of at least one of the plurality of fingers, wherein at least one of the additional stress-reducing ridges is disposed on the back surface of the thumb,
wherein a flexing of a human hand when wearing the polymeric glove articulates the at least one additional stress-reducing ridge and first stress-reducing ridge without having to significantly stretch the polymeric glove, and
wherein the two peaks of the first stress-reducing ridge or at least one additional stress-reducing ridge have radius of curvature of approximately 8-9 mm and the one valley has a radius of curvature of approximately 5-6 mm.

2. The polymeric glove of claim 1, wherein a placement of the at least one additional stress-reducing ridge is adapted to correspond to at least one of a distal interphalangeal joint, a proximal interphalangeal joint, and/or a metacarpophalangeal joint of the human hand of the wearer of the polymeric glove.

3. The polymeric glove of claim 1, wherein at least one of the two peaks of the first stress-reducing ridge or at least one additional stress-reducing ridge is approximately 10 mm in height from a baseline.

4. The polymeric glove of claim 1, wherein a bottom of the one valley of the first stress-reducing ridge or at least one additional stress-reducing ridge is approximately 5 mm in height from a baseline.

5. The polymeric glove of claim 1, wherein a curved length across the two peaks and the one valley disposed therebetween of the first stress-reducing ridge or at least one additional stress-reducing ridge is increased by approximately 48% compared with a polymeric glove having no ridge.

6. The polymeric glove of claim 1, wherein the first stress-reducing ridge or at least one additional stress-reducing ridge have a start point and an end point approximately 3 cm to 4.5 cm in linear length from the start point.

7. The polymeric glove of claim 1, wherein the first stress-reducing ridge provides an additional 10 sq. cm 14 sq. cm of surface area to the backhand region.

8. The polymeric glove of claim 1, wherein the at least one additional stress-reducing ridge provides an additional 0.5 sq. cm to 10 sq. cm of surface area to the back surface of the finger.

9. The polymeric glove of claim 1, wherein the one valley of the first stress-reducing ridge is perpendicular to a longitudinal axis of the polymeric glove, and wherein the one valley of the first stress-reducing ridge extends substantially across the back-hand region.

* * * * *